US00PP17864P3

(12) United States Plant Patent
Nelson et al.

(10) Patent No.: US PP17,864 P3
(45) Date of Patent: Jul. 17, 2007

(54) STRAWBERRY PLANT NAMED 'BG-959'

(50) Latin Name: *Fragaria ananassa*
Varietal Denomination: BG-959

(75) Inventors: Steven D. Nelson, Watsonville, CA (US); Michael D. Nelson, Watsonville, CA (US); Lee W. Stoeckle, Ventura, CA (US)

(73) Assignee: Berry Genetics, Inc., Freedom, CA (US)

( * ) Notice: Subject to any disclaimer, the term of this patent is extended or adjusted under 35 U.S.C. 154(b) by 195 days.

(21) Appl. No.: 11/099,470

(22) Filed: Apr. 6, 2005

(65) Prior Publication Data

US 2006/0230479 P1 Oct. 12, 2006

(51) Int. Cl.
*A01H 5/00* (2006.01)

(52) U.S. Cl. ..... Plt./208

(58) Field of Classification Search ..... Plt./208
See application file for complete search history.

(56) References Cited

PUBLICATIONS

European Union Community Plant Variety Office (CPVO) 2005/0799 filed Apr. 29, 2005—documents include a copy of the Filing Receipt received from the CPVO dated Jun. 20, 2005 verifying application information (2 pgs.).
Mexican Plant Breeder's Rights Application 621 filed Oct. 10, 2005—documents include a copy of the Filing Receipt verifying application information (5 pgs.) and Plant Variety Rights Application Papers (16 pgs.).
Morroco—Copy of e–mail transmission from a representative of the foreign associate Algemeen Octrool–En Merkenbureau verifying submission of an application (no filing details available at this time) (3 pgs.).

*Primary Examiner*—Kent Bell
*Assistant Examiner*—Annette H Para
(74) *Attorney, Agent, or Firm*—Foley & Lardner LLP

(57) ABSTRACT

This invention relates to a new and distinct short-day variety of strawberry plant named 'BG-959'. This new variety is primarily adapted to the growing conditions of the southern coast of California. A small plant with large uniformly shaped berries primarily characterizes the new variety. Foliage is small in size with short petioles producing very few bract leaflets. Production is early beginning as early as late December, producing upwards of 20% of 25% of it production by the end of February. The fruit is large in size, very firm, flat conical in shape with a smooth surface lacking creases and ridges.

5 Drawing Sheets

Botanical designation: *Fragaria ananassa.*
Variety denomination: 'BG-959'.

BACKGROUND OF THE INVENTION

The present invention relates to a new and distinct short-day strawberry variety designated as 'BG959'. This new variety is a result of a controlled cross made by the Inventors, Steven D. Nelson, Michael D. Nelson and Lee W. Stoeckle, in 1996 between 'Camarosa' (U.S. Plant Pat. No. 8,708) and 'PS-1269' (U.S. Plant Pat. No. 10,686). The variety is botanically known as *Fragaria ananassa.*

The seedling resulting from the aforementioned cross was asexually propagated by stolons in a nursery located in Siskiyou County, Calif., and was subsequently selected by the Inventors from a controlled breeding plot near Oxnard, Calif. in 1998. After its selection, the new variety was further asexually propagated by stolons in both Siskiyou County, Calif. and San Joaquin County, Calif. The new variety was extensively tested over the next several years in fruiting fields near Oxnard, Calif. This propagation has demonstrated that the combination of traits disclosed herein as characterizing the new variety are fixed and remain true to type through successive generations of asexual reproduction.

BRIEF SUMMARY OF THE INVENTION

'BG-959' is primarily adapted to the climate and growing conditions of the southern coast of California. This region provides the necessary winter temperatures required for it to produce a strong vigorous plant and to remain in fruit production from January through June. The nearby Pacific Ocean provides the needed humidity and moderate temperatures to maintain fruit quality during the winter and spring production months.

The following traits have been repeatedly observed and are determined to be the unique characteristics of 'BG-959'. These characteristics in combination distinguish 'BG-959' as a new and distinct cultivar:

1. a small plant with large uniformly shaped berries;
2. foliage small in size with short petioles producing very few bract leaflets;
3. fruit large in size, very firm, and flat conical in shape with a smooth surface lacking creases and ridges;
4. production of cultivar is early beginning as early as late December, producing upwards of 20% to 25% of it production by the end of February; and
5. cultivar is primarily adapted to the growing conditions of the southern coast of California.

The varieties that are believed to be most closely related to 'BG-959' are 'BG-269' (U.S. Plant Pat. No. 12,628) and parental cultivar 'Camarosa' (U.S. Plant Pat. No. 8,708).

In comparison to the similar varieties 'BG-269' and 'Camarosa', 'BG-959' differs by the following combination of characteristics as described in Table 1:

TABLE 1

| Characteristic | 'BG-959' | 'BG-269' (PP12,628) | 'Camarosa' (PP8,708) |
|---|---|---|---|
| Plant | | | |
| Size | small | large | medium |
| Vigor | weak | strong | medium |
| Foliage/Petioles | | | |
| Leaf size | medium-small | medium-large | medium |
| Frequency of bract leaflets | 5–10% | 60–70% | 2–6% |
| Petiole length | short | long | long |
| Petiolule length | short | long | medium |
| Stipule length | short | long | medium |
| Fruit | | | |
| Size | medium-large | large-very large | medium-large |
| L/W ratio | slightly longer than broad | slightly broader than long | much longer than broad |
| Shape | conical-flat conical | conical-rounded | cylindrical-wedged |
| Band without achenes | narrow | absent or very narrow | medium |
| Unevenness of surface | absent or very weak | medium | medium-strong |
| Glossiness | medium-strong | medium-strong | medium-weak |
| Insertion of achenes | level with surface | level with surface | below surface |
| Flesh firmness | firm-very firm | medium | very firm |
| Inflorescences | | | |
| Position relative to foliage | level with | level with to above | level with to beneath |
| Fruiting truss length | short | medium | short |
| Time of ripening | early-very early | medium-early | early-very early |

For identification a series of molecular markers have been determined for this new variety.

BRIEF DESCRIPTIONS OF THE DRAWINGS

The accompanying color photographs show typical specimens of the new variety 'BG-959' at various stages of development as true as is reasonably possible with color reproductions of this type. Color in the photographs may differ slightly from the color value cited in the botanical description which accurately describe the color of 'BG-959'. The depicted plant and plant parts were taken from Oxnard, Calif. and are approximately 5 to 6 months old:

DETAILED BOTANICAL DESCRIPTION

Figure 1:
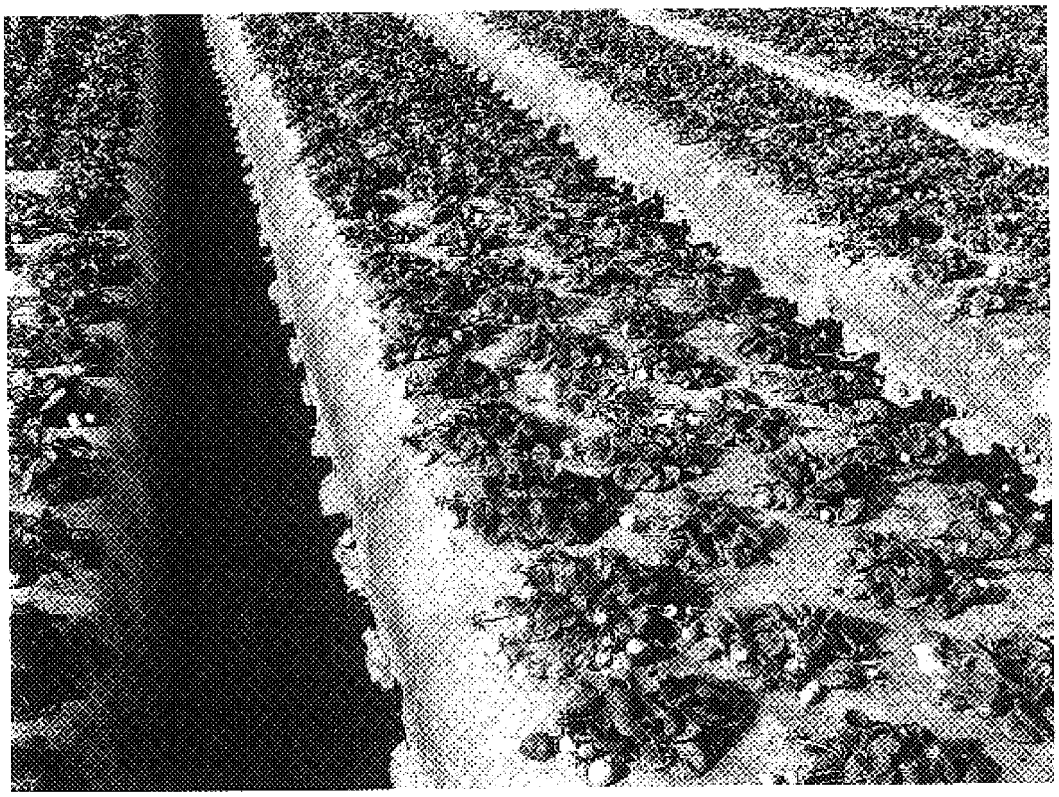
FIG. 1 shows typical fruiting field characteristics on Mar. 18, 2003.
Figure 2:
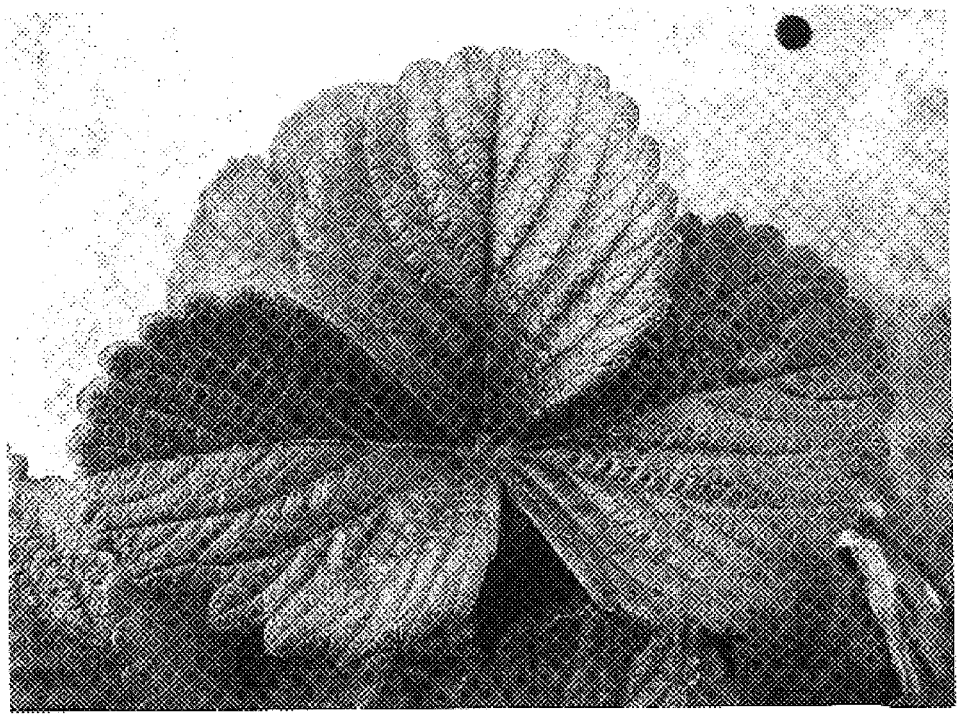
FIG. 2 shows a close-up view of a typical mature trifoliate on Mar. 2, 2005.
Figure 3:
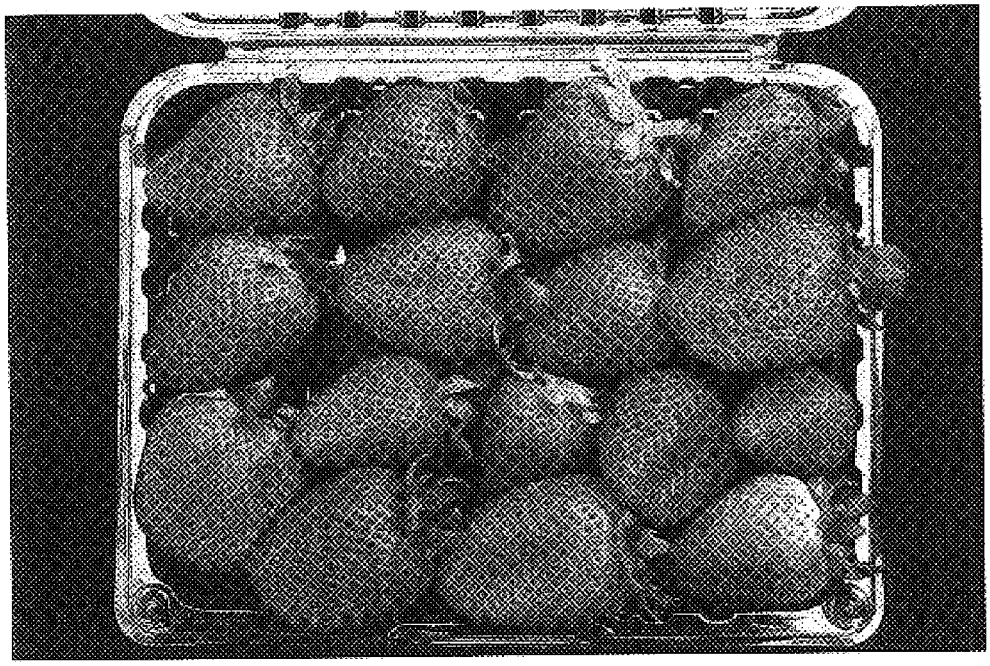
FIG. 3 shows a close-up view of fruit on Mar. 22, 2002.
Figure 4:
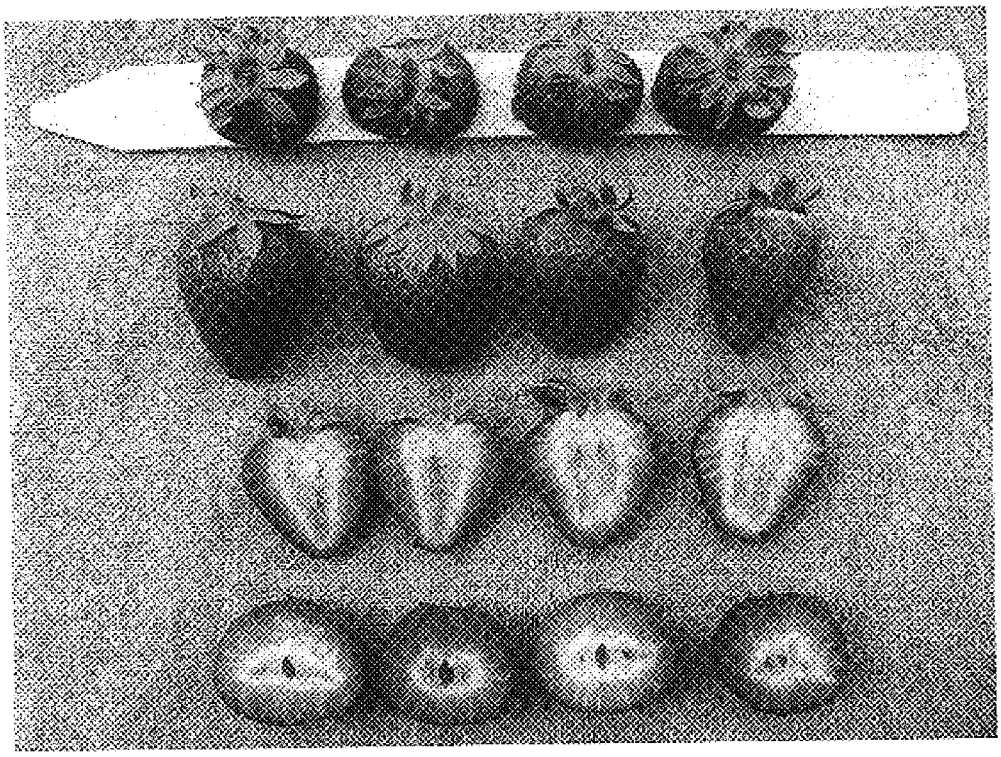
FIG. 4 shows typical internal and external fruit characteristics on Apr. 3, 2003.
Figure 5:
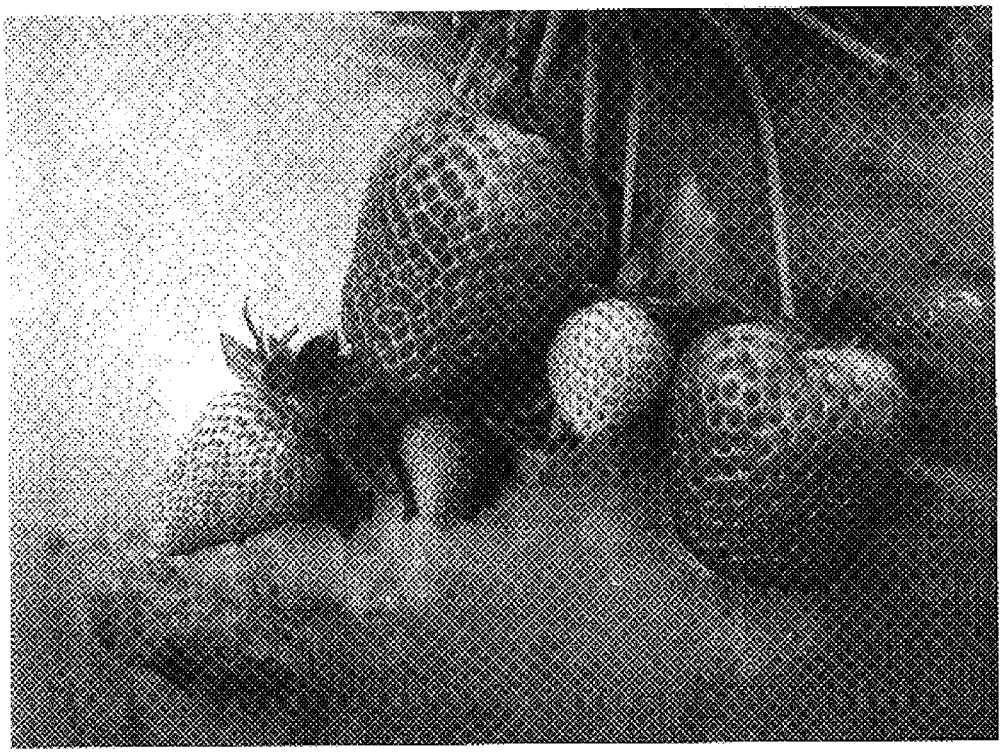
FIG. 5 shows typical mature and immature field fruit on Mar. 2, 2005.

The following description of 'BG-959' unless otherwise noted, is based on observations taken during the 2003 growing season in Oxnard, Calif. These measurements and ratings were taken from plants dug from a high-elevation nursery located in Siskiyou County, Calif. during the first week of October 2002 and planted 5 days later in Oxnard, Calif. The approximate age of the observed plants is 5 to 6 months. Yield observations and fruit quality characteristics are averaged from four years of data collected from the 2001 through the 2004 growing seasons. The characteristics of the new variety may vary in detail, depending upon variations in environmental factors, including weather (temperature, humidity and light intensity), day length, soil type and location. 'BG-959' has not been observed under all possible environmental conditions. Color terminology follows the Munsell Book of Colors, Munsell Color, Baltimore, Md. (1976).

Fruit Characteristics

Tables 2, 3 and 4 describe fruit, fruit production and fruit quality characteristics of 'BG-959'. Characteristics are taken from secondary fruit on a first year planting.

TABLE 2

2000–2004 market fruit yield and fruit size characteristics of 'BG-959' with standards from Oxnard, Calif.

| Cultivar | 2000–2004 Average Fresh Yield GM/PL | 2000–2004 Average Freezer Yield GM/PL | 2000–2004 Average Fruit Size GRM |
|---|---|---|---|
| 'BG-959' | 672 | 256 | 26.8 |
| 'BG-269' | 874 | 246 | 30.5 |
| 'Camarosa' | 648 | 250 | 25.6 |

Fruit was harvested from January through June 2000–2004. The plants of 'BG-959' were dug from a high elevation nursery (Macdoel, Calif.) during the first week of October and planted approximately 3 to 4 days later in Oxnard, Calif. 'BG-959' is compared with standards dug and planted comparably.

TABLE 3

Comparison of 2001–2004 fruit quality characteristics, including flavor and soluble solids of 'BG-959', with standards from Oxnard, Calif.

| Character | 'BG-959' | 'BG-269' | 'Camarosa' |
|---|---|---|---|
| Skin Firmness* | 8.2 | 8.0 | 8.3 |
| Fruit Appearance* | 7.7 | 7.6 | 6.3 |
| Friut Gloss* | 8.0 | 8.0 | 7.5 |
| Flavor** | 2.6 | 3.0 | 2.4 |
| Soluble Solids*** | 7.4 | 8.0 | 7.5 |

*Results are averaged from 4 years of data collected from January through May 2001–2004. Ratings are based on a scale from 1–10; the higher the rating, the stronger the skin and more attractive and glossy the berry.
**Results are averaged from 3 years of data collected from March through May 2002–2004. Ratings are based on a scale from 1–5; the higher the rating the better the flavor.
***Results are averaged from 3 years of data collected from March through May 2002–2004. Soluble solid content is measured in percent Brix, with percent Brix being an indirect measurement of the sugar content in the fruit.

TABLE 4

Comparison of secondary fruit characteristics of 'BG-959', with standards from Oxnard, Calif., Mar. 19, 2003.

| Character | 'BG-959' | 'BG-269' | 'Camarosa' |
|---|---|---|---|
| Munsell Color Range | 7.5R 3/8 to 4/10 | 7.5R 2/8 to 3/8 | 5R 3/8 to 3/10 |
| Mature Fruit | | | |
| Friut Length mean (cm) | 4.39 | 4.07 | 4.69 |

TABLE 4-continued

Comparison of secondary fruit characteristics of 'BG-959', with standards from Oxnard, Calif., Mar. 19, 2003.

| Character | 'BG-959' | 'BG-269' | 'Camarosa' |
|---|---|---|---|
| Fruit Width mean (cm)* | 4.03 | 4.29 | 3.75 |
| Fruit Length/ Width Ratio | 1.10 | 0.95 | 1.25 |
| Calyx Diameter mean (cm) | 4.4 | 5.2 | 4.6 |
| No. Sepals/Berry | 11.6 | 13.2 | 11.8 |
| Seed Weight mean (mgs) | 0.50 | 0.50 | 0.67 |

*Width is measured across the widest part of the berry, typically across the shoulders Fruit:

*Ratio of length/width.*—Slightly longer than broad.
*Size.*—Medium to large.
*Predominant shape.*—Conical to flat conical.
*Difference in shapes between primary and secondary fruit.*—Slight to moderate.
*Band without achenes.*—Narrow.
*Unevenness of surface.*—Absent or very weak.
*Color of mature fruit.*—Red, (4.5R 3/8 to 4/10).
*Evenness of color.*—Slightly uneven to even.
*Glossiness.*—Medium to strong.
*Insertion of achenes.*—Level with surface.
*Insertion of calyx.*—In basin to level with.
*Attitude of the calyx segments.*—Collapsing.
*Size of calyx in relation to fruit diameter.*—Slightly larger.
*Adherence of calyx (when fully ripe).*—Strong.
*Firmness of skin.*—Very firm.
*Firmness of flesh.*—Firm to very firm.
*Color of flesh.*—Medium red (75.1R 4/12 to 4/14).
*Distribution of red color of the flesh.*—Marginal and central.
*Hollow center.*—Moderately expressed.
*Seed color.*—Medium yellow to medium red (5Y 6/8 to 7.5R 3/8).
*Time of flowering (50% of plants at first flower).*—Very early to early.
*Time of ripening (50% of plants with ripe fruit).*—Very early to early.
*Type of bearing.*—Not remontant.

Plant Characteristics

Table 5 describes plant characteristics of 'BG-959'. Characteristics are taken from a fully mature mid season plant.

TABLE 5

Comparison of plant characteristics of 'BG-959', with standards from Oxnard, Calif., Mar. 19, 2003.

| Character | 'BG-959' | 'BG-269' | 'Camarosa' |
|---|---|---|---|
| Plant Height mean (cm) | 10.8 | 15.3 | 14.2 |
| Plant Spread mean (cm) | 24.4 | 28.7 | 27.2 |
| Crowns/Plant (mean) | 2.6 | 2.8 | 2.7 |

Plant:

*Size.*—Small.
*Habit.*—Flat globose.
*Density.*—Medium.
*Vigor.*—Weak to medium.

Stolons:

*Number.*—Medium to few.
*Anthocyanin coloration.*—Medium.
*Thickness.*—Medium to thin.
*Pubescence.*—Medium.

Foliage Characteristics

Table 6 describes foliage characteristics of 'BG-959'. Characteristics are taken from a fully mature tri-foliate during mid season.

TABLE 6

Comparison of leaf characteristics of 'BG-959', with standards from Oxnard, Calif., Mar. 19, 2003.

| Character | 'BG-959' | 'BG-269' | 'Camarosa' |
|---|---|---|---|
| Munsell Color Range (upper surface) | 7.5GY 3/4 to 3/6 | 7.5GY 3/4 to 3/6 | 5GY 3/4 to 3/6 |
| Terminal Leaflet Length mean (cm) | 5.7 | 6.7 | 6.3 |
| Terminal Leaflet Width mean (cm) | 5.3 | 5.8 | 5.7 |
| Terminal Leaflet ratio (L/W) | 1.08 | 1.2 | 1.1 |
| Petiole Length mean (cm) | 7.6 | 9.7 | 9.7 |
| Petiole Width mean (mm) | 2.8 | 3.1 | 2.8 |
| Petiolule Length mean (mm) | 3.6 | 9.2 | 6.0 |
| Serrations/Leaf | 18.8 | 21.0 | 17.7 |
| Serration Depth mean (mm) | 3.2 | 3.4 | 4.2 |
| Stipule Length mean (cm) | 1.1 | 1.9 | 1.4 |
| Stipule Width mean (cm) | 1.2 | 1.2 | 1.1 |

Foliage:

*Color of upper surface.*—Medium green, (7.5GY 3/4 to 3/6).
*Color of under side.*—Medium gray green (7.5GY 5/4 to 6/4).
*Shape in cross section.*—Slightly concave to slightly convex.
*Blistering.*—Medium to strong.
*Glossiness.*—Medium to strong.
*Number of leaflets/leaf.*—Three.

Terminal leaflet:

*Size.*—Medium to small.
*Length/width ratio.*—As long as broad to longer than broad.
*Shape of base.*—Obtuse.
*Shape of incision of margins.*—Rounded.

Petiole:

*Pubescence.*—Heavy.
*Stipule color.*—Medium green, (2.5GY 6/6 to 6/8).
*Anthocyanin coloration of stipule.*—Medium to strong.
*Attitude of hairs.*—Strongly outward.
*Frequency of bract leaflets.*—Few (occur on approx 5-10% of petioles).

Flowers and Inflorescences

Table 7 describes inflorescence and flower characteristics of 'GB-959'. Inflorescence characteristics are taken from a fully mature plant while flower characteristics are taken from a secondary flower during mid season.

TABLE 7

Comparison of inflorescence and secondary flower characteristics of 'BG-959', with standards from Oxnard, Calif., Mar. 19, 2003.

| Character | 'BG-959' | 'BG-269' | 'Camarosa' |
|---|---|---|---|
| Fruiting Truss Length* mean (cm) | 19.1 | 24.3 | 21.0 |
| Corola Diameter mean (cm) | 3.2 | 3.3 | 3.0 |
| Calyx Diameter mean (cm) | 3.6 | 3.7 | 3.4 |
| Petal Length mean (cm) | 1.3 | 1.3 | 1.1 |
| Petal Width mean (cm) | 1.2 | 1.4 | 1.1 |
| Petal L/W Ratio | 1.08 | 0.93 | 1.0 |
| Petals/Flower (mean) | 5.7 | 6.7 | 5.5 |
| Sepal Length mean (cm) | 1.4 | 1.4 | 1.3 |
| Sepal Width mean (cm) | 0.7 | 0.5 | 0.6 |
| Sepal L/W Ratio | 2.0 | 2.8 | 2.2 |
| Sepals/Flower (mean) | 11.0 | 13.1 | 11.3 |

*As measured from the base of the primary peduncle where it attaches to the crown of the plant to the furthest berry.

Inflorescence:

*Position relative to foliage.*—Level with.

*Pubescence.*—Medium.

*Anthocyanins.*—Moderate to strong.

Flowers:

*Color.*—White, (N 9.25/84.2% R to N 9/78.7% R).

*Size.*—Large.

*Size of calyx relative to corolla.*—Larger.

*Relative position of petals.*—Touching to overlapping.

*Petal length/width ratio.*—Longer than broad.

Pest Reactions

This new variety may not be resistant to any of the known insects, diseases or viruses common in California. It is known to be tolerant to the two-spotted spider mite, aphid and flower thrips when treated properly. It is also known to be moderately tolerant to grey fruit mold, powdery mildew and susceptible to angular leaf spot. The susceptibility of the new variety to any of the virus complexes of California has not been determined.

We claim:

1. A new and distinct strawberry plant named 'BG-959', as herein described and illustrated by the characteristics set forth above.

* * * * *